(12) United States Patent
Silkaitis (10) Patent No.: US 10,759,564 B2
(45) Date of Patent: Sep. 1, 2020

(54) DISPLAY DEVICE WITH SAMPLE DISPENSER AND CORRESPONDING SYSTEMS AND METHODS

(71) Applicant: Medline Industries, Inc., Northfield, IL (US)

(72) Inventor: Thomas Silkaitis, Lake Zurich, IL (US)

(73) Assignee: Medline Industries, Inc., Northfield, IL (US)

( * ) Notice: Subject to any disclaimer, the term of this patent is extended or adjusted under 35 U.S.C. 154(b) by 113 days.

(21) Appl. No.: 15/492,456

(22) Filed: Apr. 20, 2017

(65) Prior Publication Data
US 2018/0305080 A1     Oct. 25, 2018

(51) Int. Cl.
| | | |
|---|---|---|
| B65D 25/00 | (2006.01) | |
| B65D 5/42 | (2006.01) | |
| B65D 1/22 | (2006.01) | |
| B65D 5/30 | (2006.01) | |
| B65F 1/02 | (2006.01) | |
| A61B 42/40 | (2016.01) | |
| B65D 83/08 | (2006.01) | |
| B65D 5/48 | (2006.01) | |
| B65D 5/52 | (2006.01) | |

(52) U.S. Cl.
CPC ............ B65D 25/005 (2013.01); A61B 42/40 (2016.02); B65D 1/22 (2013.01); B65D 5/302 (2013.01); B65D 5/4212 (2013.01); B65D 5/48012 (2013.01); B65D 5/52 (2013.01); B65D 83/0888 (2013.01); B65F 1/02 (2013.01); B65D 83/0805 (2013.01); B65F 2220/102 (2013.01); B65F 2250/108 (2013.01); B65F 2250/114 (2013.01)

(58) Field of Classification Search
CPC ...... B65D 25/005; B65D 1/22; B65D 5/5286; B65D 5/302; B65D 5/4212; B65D 5/48012; B65D 83/088; A61B 42/40; B65F 1/02; B65F 2220/102; B65F 2250/108; B65F 2250/114
USPC ..................... 206/730–736; 312/118; 211/63
See application file for complete search history.

(56) References Cited

U.S. PATENT DOCUMENTS

| | | | | |
|---|---|---|---|---|
| 720,345 | A * | 2/1903 | Hazeltine | ............... B65D 5/029 206/557 |
| 1,099,832 | A * | 6/1914 | Warren | ..................... A47F 3/00 206/730 |
| 2,278,914 | A * | 4/1942 | Cowles | ................ B65D 5/5286 206/733 |

(Continued)

OTHER PUBLICATIONS

"Photo of Display Box", Medline Display Box; SensiCare Ice—shown displaying Curad Exam Gloves; Unknown Publication Date but prior to filing of present application.

(Continued)

*Primary Examiner* — Chun Hoi Cheung
(74) *Attorney, Agent, or Firm* — Philip H. Burrus, IV (57) ABSTRACT

A display container (200) includes one or more sidewalls (102,103,107) defining a receiving recess (207). A dispenser (201) can define a front side of the display container. Where this is the case the dispenser has a height (208) less than the one or more sidewalls. The dispenser includes an aperture (324). A plurality of sample product, such as disposable gloves (210) can be placed within the dispenser. One or more packages (203,204,205,206) of product corresponding to the sample product can be situated within the receiving recess.

20 Claims, 6 Drawing Sheets

(56) References Cited

U.S. PATENT DOCUMENTS

| | | |
|---|---|---|
| 3,171,347 A | 3/1965 | Elrod |
| 3,243,079 A * | 3/1966 | Rettmer ............. B65D 83/0811 |
| | | 221/63 |
| D251,360 S | 3/1979 | Collin |
| D256,642 S | 9/1980 | Lovell |
| D263,121 S | 2/1982 | Lowry |
| D277,532 S | 2/1985 | Duhamel |
| D288,394 S | 2/1987 | Canter |
| 4,962,859 A | 10/1990 | Kump |
| D319,130 S | 8/1991 | Williams |
| D320,556 S | 10/1991 | Fairhurst |
| 5,092,467 A | 3/1992 | Elward |
| 5,105,945 A | 4/1992 | Carver |
| 5,251,972 A * | 10/1993 | Zurawin .................... A47F 3/14 |
| | | 312/114 |
| D344,838 S | 3/1994 | Hakansson |
| D352,855 S | 11/1994 | Wolff |
| D356,680 S | 3/1995 | Edgerton, Jr. et al. |
| D401,119 S | 11/1998 | Demore |
| 6,021,920 A * | 2/2000 | Aldape .................. A61B 42/40 |
| | | 206/233 |
| 6,149,111 A | 11/2000 | Epstein |
| D438,688 S | 3/2001 | Rastetter |
| D444,965 S | 7/2001 | Miller |
| D452,820 S | 1/2002 | Hacker |
| D457,352 S | 5/2002 | Hansen |
| 6,439,386 B1 * | 8/2002 | Sauer .................... B65D 5/4208 |
| | | 206/494 |
| D469,974 S | 2/2003 | Scribner |
| 6,520,339 B1 * | 2/2003 | Conway, Jr. ........... B65D 25/20 |
| | | 206/730 |
| 6,547,095 B1 * | 4/2003 | Emoff .................... B65D 83/12 |
| | | 206/812 |
| D474,923 S | 5/2003 | Johnson |
| D477,915 S | 8/2003 | Slight |
| D479,062 S | 9/2003 | Meyer |
| D513,757 S | 1/2006 | Grobleben |
| D529,311 S | 10/2006 | Waldron |
| 7,422,296 B2 | 9/2008 | Williquette et al. |
| 7,731,085 B2 * | 6/2010 | Gillespie .................... A47F 1/04 |
| | | 221/155 |
| D622,989 S * | 9/2010 | Lagler ............................ D6/515 |
| 8,025,187 B2 | 9/2011 | Sottosanti, Jr. et al. |
| D666,903 S | 9/2012 | McIntosh et al. |
| D689,718 S | 9/2013 | Puckett |
| D697,793 S | 1/2014 | Levy et al. |
| D715,641 S | 10/2014 | Spinos |
| D781,625 S | 3/2017 | Poniatowski |
| D783,395 S | 4/2017 | Wang |
| D786,588 S | 5/2017 | Knapp |
| D795,060 S | 8/2017 | Talios et al. |
| D837,577 S * | 1/2019 | Silkaitis ........................ D6/683 |
| 2006/0186184 A1 | 8/2006 | Jourdain |
| 2007/0045333 A1 * | 3/2007 | Mitchell ............... A47K 10/424 |
| | | 221/34 |
| 2008/0308572 A1 | 12/2008 | Gillespie et al. |
| 2010/0163569 A1 * | 7/2010 | Parker ................. A47K 10/3818 |
| | | 221/1 |
| 2012/0279992 A1 | 11/2012 | Wilder |
| 2013/0146501 A1 * | 6/2013 | Zusmanis ................. B65F 1/06 |
| | | 206/525 |
| 2013/0228589 A1 * | 9/2013 | Nickerson ............... A47K 10/46 |
| | | 221/102 |
| 2016/0338487 A1 | 11/2016 | McGrane et al. |

OTHER PUBLICATIONS

Donnelly, Kelley, "Notice of Allowance", U.S. Appl. No. 29/601,239, filed Apr. 20, 2017; dated Aug. 24, 2018.

Donnelly, Kelley A., "Ex Parte Quayle", U.S. Appl. No. 29/601,239, filed Apr. 20, 2017; dated Apr. 9, 2018.

Donnelly, Kelley A., "Notice of Allowance", U.S. Appl. No. 29/671,979, filed Nov. 30, 2018; dated Jan. 31, 2019.

* cited by examiner

DISPLAY DEVICE WITH SAMPLE DISPENSER AND CORRESPONDING SYSTEMS AND METHODS

BACKGROUND

Technical Field

This invention relates generally to containers, and more particularly to containers for displays.

Background Art

In retail environments, it is often desirable to have products displayed where customers can readily and easily see their packaging. Manufacturers typically try to make retail display containers and systems as eye-catching as possible in an effort to lure customers to select their products for purchase. Manufacturers also compete with rivals to have products situated at "premiere" shelf locations so that they are readily accessible to customers. At the same time, merchants frequently want to offer a wide variety of products to consumers.

These competing forces frequently leave shelves packed with goods. There is little room for anything other than the product itself. Accordingly, manufacturers wanting to offer coupons, purchase incentives, samples, or other "extras" are left without any spare space with which to make such offerings. Moreover, where the product is packaged in a box or other container, a customer may be precluded from inspecting or viewing the actual product itself due to the limited amount of shelf space. It would be advantageous to have improved display systems and methods capable of more efficiently using shelf space.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. It is expected that one of ordinary skill, notwithstanding possibly significant effort and many design choices motivated by, for example, available time, current technology, and economic considerations, when guided by the concepts and principles disclosed herein will be readily capable of generating embodiments configured in accordance with the disclosure. The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Also, reference designators shown herein in parenthesis indicate components shown in a figure other than the one in discussion. For example, talking about a device (10) while discussing figure A would refer to an element, 10, shown in figure other than figure A.

As noted above, when products are packaged on a shelf in a retail setting, it may be difficult or impossible for a prospective customer to view or inspect the product itself. This is especially true where a customer relies upon a product being properly fitted. Using a glove as an example, nitrile, latex, silicon, or other disposable gloves are generally packaged in boxes or sealed packages. Some are even specially packaged to preserve sterility. It can be challenging for a customer contemplating the purchase of gloves or other fitted products to determine whether a particular size fits.

In addition to fit, products such as gloves, socks, shirts, or shorts may have other features that the customer wishes to examine prior to purchase. Using gloves again as an example, a particular glove may have a defined thickness, texture, material, durability, softness, stretchiness, smoothness, and/or coating or additive. The customer may wish to examine these attributes prior to purchase. If the customer is in a "big box" retail store or wholesale warehouse store, an erroneous purchase may result in the customer procuring a very large quantity of ill-fitting or ill-suited product. Where shelf space is limited or product packaging serves as a constraint, the customer may simply not be able to examine important features of the product prior to purchase.

Embodiments of the disclosure solve this problem by providing a display container that includes a dispenser for product samples. In one or more embodiments, a display container is configured to hold one or more packages of a particular product. Illustrating by example, in one embodiment the display container is configured to hold one or more boxes of disposable gloves.

In one embodiment, a dispenser for product samples forms the front facing panel of the tray. In one embodiment, a walled cavity is defined within the display container. The walled cavity defines an aperture. One or more product samples can be placed within the walled cavity. A prospective customer can withdraw one or more product samples from the walled cavity through the aperture. In some embodiments, a disposal receptacle is included within the walled cavity as well. Where included, a prospective customer may withdraw a product sample from the walled cavity through a first aperture. After trying on and/or examining the product sample, the prospective customer may discard the product sample in the disposal receptacle by passing the used sample through another aperture into a disposal cavity of the walled cavity. Accordingly, the user may examine the product and discard it in the same display container, thereby eliminating the need for a retailer to provide a separate trashcan or disposal receptacle to avoid discarded products from littering the floor.

In one or more embodiments, a display container comprises one or more sidewalls defining a receiving recess. In one embodiment, a dispenser defines a front side of the display container. In one embodiment, the dispenser has a height less than the one or more sidewalls. In other embodiments, the dispenser is coupled to one of the sidewalls.

In one or more embodiments, a plurality of sample product disposed within the dispenser. In one embodiment used herein for illustration, the sample product comprises disposable gloves. One or more packages of product corresponding to the plurality of sample product are then situated within the receiving recess. In addition to the dispenser, a disposal receptacle can be located adjacent to the dispenser. Advantageously, embodiments of the disclosure allow a prospective customer to take a sample from the dispenser, examine it for size, touch, feel, or other factors, and discard the same in the disposal receptacle to determine whether they should purchase the packaged product.

Figure 1:
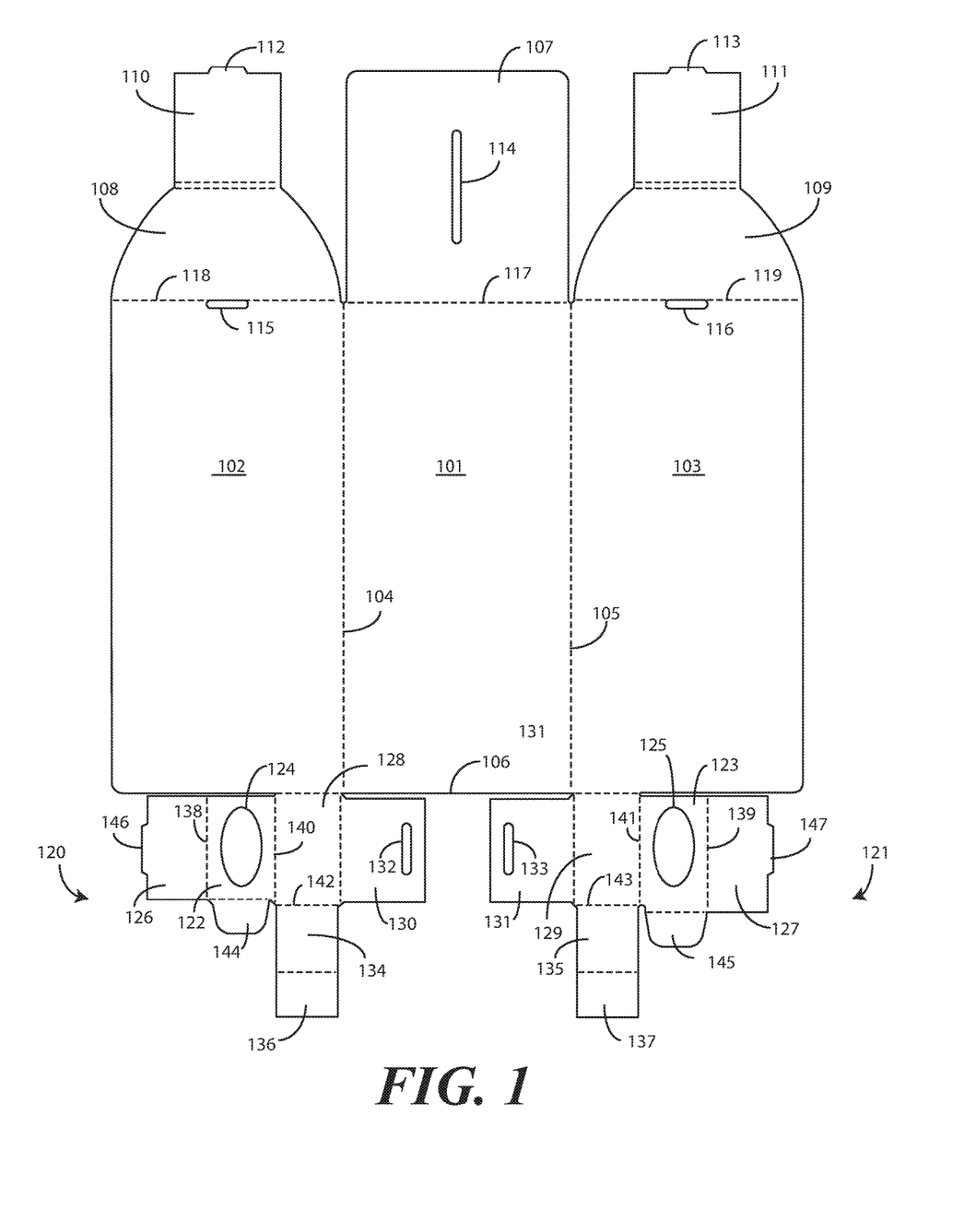
FIG. 1 illustrates one explanatory die template for a display container in accordance with one or more embodiments of the disclosure.

Turning now to FIG. 1, illustrated therein is one explanatory blank 100 suitable for making one or more display containers configured in accordance with one or more embodiments of the disclosure. The blank 100 may be manufactured from any of a variety of materials or combinations of materials, including paper, cardboard, plastic, metal, or fabric. In the illustrative embodiment of FIG. 1, the blank 100 is manufactured from single-ply cardboard. Where the blank 100 is manufactured from plastic, the plastic may be a thermoform plastic or other rigid plastic and may be transparent, semi-transparent or non-transparent. Regardless of whether cardboard, metal, plastic, or fabric, the blank 100 may be of any desired color, and may include printing. Other materials will be obvious to those of ordinary skill in the art having the benefit of this disclosure. The blank 100 may have letters, pictures, logos, designs, instructions for using the contents therein, and/or other markings placed thereon through printing, engraving, molding, or any other suitable method.

In the illustration shown in FIG. 1, the solid lines indicate lines that are cut during the die cutting process. By contrast, the dashed lines show lines that are folded in the method steps of manufacturing the display container. In one or more embodiments, the blank 100 is die cut from a thin sheet of cardboard. In another embodiment, the blank 100 is die cut from a thin sheet of plastic. In another embodiment, the blank 100 is die cut from a thin sheet of stiff paper or poster board. In one or more embodiments, the blank 100 is die cut form a planar sheet of material and has a rigidity suitable for holding one or more items when folded into a display container.

In one or more embodiments, a bottom panel 101 is bounded on two sides by a first sidewall 102 and a second sidewall 103. In this illustrative embodiment, a first transverse fold line 104 separates the first sidewall 102 from the bottom panel 101, while a second transverse fold line 105 separates the second sidewall 103 from the bottom panel 101. The bottom panel 101 is also bounded by a bottom edge 106 and a rear sidewall 107.

In one or more embodiments, each of the first sidewall 102 and the second sidewall 103 are bounded at the rear of the blank 100 by a first arched partial rear sidewall 108 and a second arched partial rear sidewall 109, respectively. As illustrated in FIG. 1, the first arched partial rear sidewall 108 extends distally from the first sidewall 102 toward the rear of the blank 100. Similarly, the second arched partial rear sidewall 109 extends distally from the second sidewall 103 toward the rear of the blank 100.

In this illustrative embodiment, a first tab 110 extends distally from the first arched partial rear sidewall 108, while a second tab 111 extends distally from the second arched partial rear sidewall 109. The first tab 110 terminates in a first insertion tab 112, while the second tab 111 terminates at a second insertion tab 113. Said differently, in one or more embodiments, the first tab 110 is disposed between the first insertion tab 112 and the first arched partial rear sidewall 108, while the second tab 111 is disposed between the second insertion tab 113 and the second arched partial rear sidewall 109.

Turning now to the front side of the blank 100, in this illustrative embodiment each of the first sidewall 102 and the second sidewall 103 has an assembly extending therefrom. In this illustrative embodiment, the first sidewall 102 has a dispenser assembly 120 extending therefrom, while the second sidewall 103 has a disposal receptacle assembly 121 extending therefrom.

Each of the dispenser assembly 120 and the disposal receptacle assembly 121, in one embodiment, includes a top panel 122,123 defining an aperture 124,125. In this illustrative embodiment, the aperture 124,125 is ovular. However, other shapes can be used as well. In another embodiment, each aperture 124,125 is rectangular. In yet another embodiment, each aperture 124,125 is circular. Other shapes for the apertures 124,125 will be obvious to those of ordinary skill in the art having the benefit of this disclosure.

Extending from the top panel 122,123 is a first side extension 126,127 and a second side extension 128,129. Extending from the second side extension 128,129 is a bottom side extension 130,131. The bottom side extension 130,131 defines an ovular aperture 132,133. A front sidewall 134,135 extends distally from the second side extension 128,129 as well. In this illustrative embodiment, the front sidewall 134,135 extends from a first side of the second side extension 128,129, while the bottom side extension 130,131 extends from a second side of the second side extension 128,129. Each front sidewall 134,135 terminates at a double-wall member 136,137.

When the display container is created, the first sidewall 102 is folded about the first transverse fold line 104 relative to the bottom panel 101. Similarly, the second sidewall 103 is folded about the second transverse fold line 105 relative to the bottom panel 101. In this illustrative embodiment, the first sidewall 102 is folded toward the second sidewall 103 and vice versa. The first sidewall 102 is folded about the first transverse fold line 104 until the first sidewall is substantially orthogonal with the bottom panel 101. Similarly, the second sidewall 103 is folded about the second transverse fold line 105 until the second sidewall 103 is substantially orthogonal with the bottom panel 101.

In this illustrative embodiment, the rear sidewall 107 defines an elongated ovular aperture 114. Additionally, the first sidewall 102 defines a first minor ovular aperture 115, while the second sidewall 103 defines a second minor ovular aperture.

Once the first sidewall 102 is folded about the first transverse fold line 104 relative to the bottom panel 101 and the second sidewall 103 is folded about the second transverse fold line 105 relative to the bottom panel 101, the rear sidewall 107 can be folded about transverse fold line 117. When this occurs, the first arched partial rear sidewall 108 and the second arched partial rear sidewall 109 can be folded about transverse fold line 118 and transverse fold line 119, respectively, toward the rear sidewall 107.

First tab 110 and second tab 111 can be passed through the elongated ovular aperture 114. First insertion tab 112 can then be seated in first minor ovular aperture 115, while second insertion tab 113 is situated in second minor ovular aperture 116, thereby constructing the rear side of the display container.

Meanwhile, the first side extension 126,127 and the second side extension 128,129 are folded about transverse fold lines 138,139,140,141 until each is substantially orthogonal with their respective top panel 122,123. Double-wall member 136,137 is folded to be orthogonal to the front sidewall 134,135, which is folded about transverse fold line 142,143. Arched tabs 144,145 are folded to be substantially orthogonal with the top panel 122,123, and are inserted within the front sidewall 134,135. Double-wall member 136,137 forms a second wall by being inserted against the interior of first side extension 126,127. Insertion tab 146 is inserted into ovular aperture 132, while insertion tab 147 is situated into ovular aperture 133. Accordingly, a dispenser and a disposal receptacle are formed. The resulting display container is shown in FIG. 2.

Figure 2:
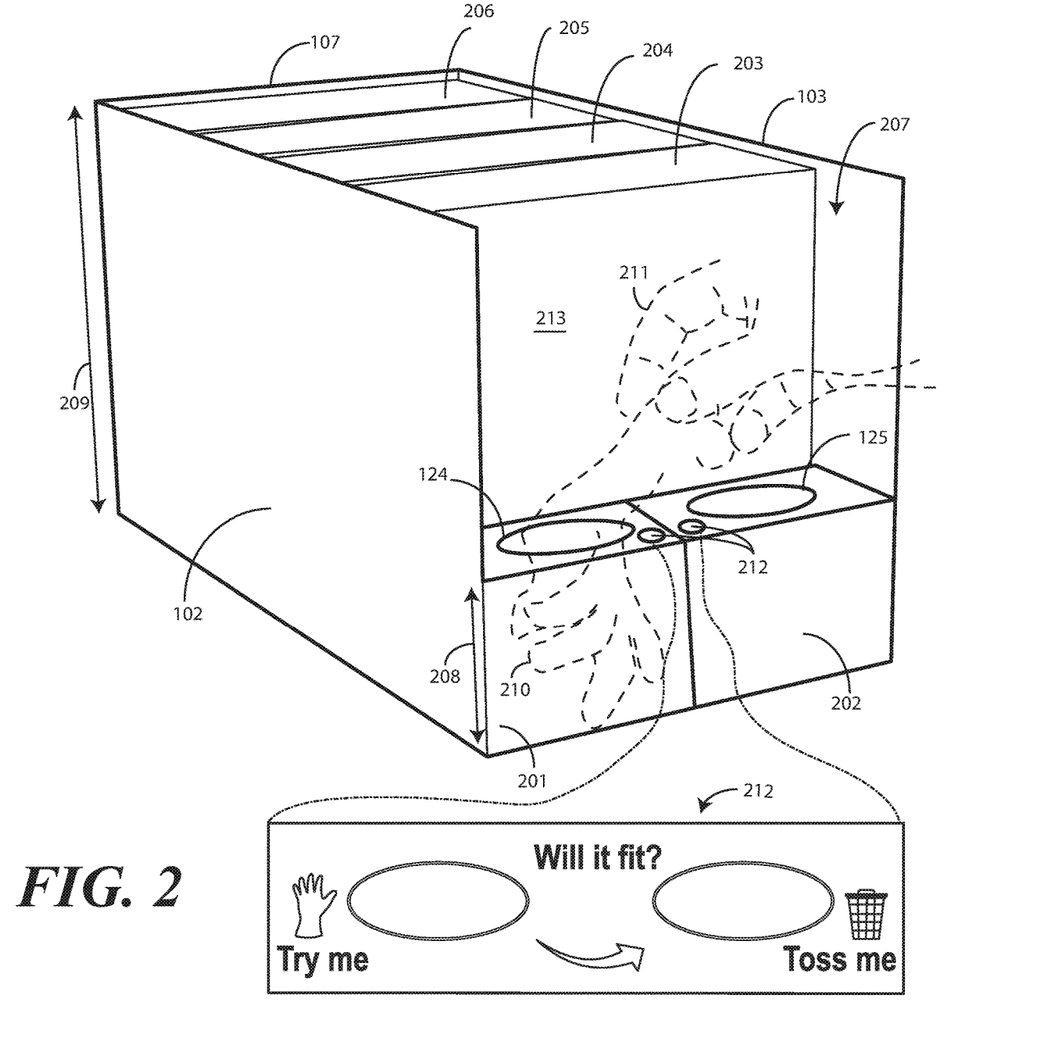
FIG. 2 illustrates one explanatory display container in accordance with one or more embodiments of the disclosure.

Turning now to FIG. 2, illustrated therein is the display container 200 formed from the blank (100) of FIG. 1. As shown the display container 200 includes a first sidewall 102, as second sidewall 103, and a rear sidewall 107. At the front of the display container 200 are the dispenser 201 formed from the dispenser assembly (120) and the disposal receptacle 202 formed from the disposal receptacle assembly (121). The combination of the dispenser 201 and the disposal receptacle 202 define the front side of the display container 200 in this illustrative embodiment.

In one embodiment, the first sidewall 102 defines a first major face of a display container 200, while the second sidewall 103 defines a second major face of the display container 200. In this illustrative embodiment, the display container 200 has a rectangular appearance due to the geometric shape of the blank (100) from which it was constructed. It will be obvious to those of ordinary skill in the art having the benefit of this disclosure that the display container 200 can be configured in other shapes as well, including cubes, cylinders, pyramids, and other shapes.

As shown, one or more packages 203,204,205,206 of products are disposed within a receiving recess 207 defined within the display container 200. In this illustrative embodiment, the packages 203,204,205,206 comprise boxes of product. In other embodiments, the packages 203,204,205, 206 can comprise pouches of products. Other containers for products, suitable for positioning within the receiving recess 207 of the display container 200, will be obvious to those of ordinary skill in the art having the benefit of this disclosure.

In one illustrative embodiment, the height 208 of the dispenser 201 and the disposal receptacle 202 is less than that of the rear sidewall 107. This allows the one or more packages 203,204,205,206 to be securely retained within the receiving recess 207 of the display container 200, while allowing the front surface 213 of the foremost package 203 to be easily visible.

While the display container 200 of FIG. 2 can be used with any number of products, in one or more embodiments the display container 200 is used with disposable gloves. Embodiments of the disclosure contemplate that disposable gloves are used to protect the hands of a user. In many industries, such as medical and surgical industries, the use of gloves is not only a protective measure, but is a requirement. Medical services personnel, for example, are required to wear disposable gloves to prevent contact with bodily fluids during surgical procedures, medical examinations, laboratory testing and other medical procedures. Disposable gloves have traditionally been made of rubber materials such as latex, thermoplastic materials such as vinyl, and other natural and synthetic materials.

Many gloves are provided in packaging where one or more gloves are disposed in an interior of a package 203, 204,205,206. In medical and other applications, a proper fit is not only a necessity, but also an imperative. A surgeon with an improper fitting glove may be impaired when practicing medicine. Similarly, even when the gloves are used for a more benign activity like cleaning restrooms, an improperly fitting glove is annoying at best, and can slide off in extreme situations.

To ensure that a prospective customer has the opportunity to examine a glove for proper fit, feature, or other characteristics, in one or more embodiments one or more sample gloves 210 are disposed within the dispenser 201. In one embodiment, the aperture 124 allows one or more gloves 210 to be drawn through the aperture 124 from the dispenser 201. Said differently, a user can remove one or more of the gloves 210 from the dispenser 201 by drawing them through the aperture 124. The aperture 124 may be configured in the form of different shapes, such as a circle, an oval, a square, a rectangle, or any variation of such shapes, such that a user may insert his or her fingers or a portion of the hand through the aperture 124 to remove one or more of the gloves 210.

In one embodiment, the aperture 124 may initially be covered by a removable segment that is initially formed as part of the display container 200. The removable segment, in one embodiment, is separable from the display container 200 by a perforation or a perforated segment. Once the container is ready for use by a user, in one embodiment the user may tear the removable segment away from the display container 200 along the perforation or perforated segment. The removable segment, where used, is generally discarded after it is removed from the display container 200. In addition to a perforated segment, the removable segment may include an adhesive segment that is removable from the display container 200 as well. The aperture 125 of the disposal receptacle 202 can be similarly covered initially in one or more embodiments.

In this illustrative embodiment, dispenser 201 defines an interior volume. One or more gloves 210 can be disposed within the interior volume such that one or more gloves 210 may be drawn from the dispenser 201 through the aperture 124. The gloves 210 may comprise medical and/or surgical gloves that are optionally disposable in one or more embodiments. Alternatively, the gloves 210 may be other types of gloves, e.g., non-medical or non-surgical gloves. Still other types of gloves suitable for use with containers configured in accordance with one or more concepts described herein will be obvious to those of ordinary skill in the art having the benefit of this disclosure.

The gloves 210 may be non-transparent, transparent or semi-transparent. Further, the gloves 210 may have any desired color. Each glove 210 can be a fingered glove with defined fingers, or alternatively a mitten style glove with one compartment for the fingers and another for the thumb. The size of the display container 200 can vary based upon the size of the gloves disposed therein.

In one embodiment, the gloves 210 are manufactured from rubber materials such as latex. In other embodiments, the gloves 210 are manufactured from thermoplastic materials such as vinyl. In still other embodiments, the gloves 210 are manufactured from and other natural and synthetic materials, such as nitrile, polyvinyl chloride, polyethylene, polyisoprene, neoprene, polychloriprene, etc. Other materials suitable for the manufacture of the gloves 210 will be obvious to those of ordinary skill in the art having the benefit of this disclosure.

In one or more embodiments, each glove 210 may comprise or include other materials, such as antimicrobial coatings and/or coatings for protecting the skin that include aloe, chamomile, vitamin(s), or combinations thereof. In other embodiments, each glove 210 may comprise other suitable ingredients that may provide skin care benefits, such as moisturizing and soothing dry, irritated skin. Other glove additives will be obvious to those of ordinary skill in the art having the benefit of this disclosure.

In one embodiment, the number of gloves 210 disposed within the dispenser 201 is related to the number of packages 203,204,205,206. For instance, where there are four packages 203,204,205,206 of gloves in the display container, there may be one to two pairs of gloves 210 within the dispenser. In one embodiment, there is one pair of gloves 210 per package 203,204,205,206 disposed within the dispenser 201. In another embodiment, there are two pairs of gloves 210 per package 203,204,205,206 disposed within the dispenser 201. In yet another embodiment, there are four pairs of gloves 210 per package 203,204,205,206 disposed within the dispenser 201. Accordingly, where the display container 200 includes five packages, there may be a range of ten to twenty gloves 210 disposed within the dispenser 201. Other numbers of sample products disposed within the dispenser 201 will be obvious to those of ordinary skill in the art having the benefit of this disclosure.

Advantageously, the dispenser 201 allows a prospective customer 211 to draw a glove 210 through the aperture 124 of the dispenser 201 to try it on for fit, as well as examine the other physical characteristics of the glove 210 to see if it is suitable for purchase. Advantageously, the aperture 124 of the dispenser 201, combined with the overall weight of the display container 200 when the packages 203,204,205, 206 of gloves are disposed therein, allows a single-handed drawing of one or more gloves 210 from the dispenser 201.

Visible indicia 212 can be disposed along one or both of the dispenser 201 or the disposal receptacle 202 to indicate the purpose and function of each feature. For example, in one embodiment the visible indicia 212 comprise the words "Try me," with those words disposed near the aperture 124 of the dispenser 201. The visible indicia 212 can also include the words "Will it fit," on one or both of the dispenser 201 or the disposal receptacle 202 to indicate that the gloves 210 disposed within the dispenser 201 are there so that the prospective customer 211 can determine whether the size is appropriate. Similarly, the visible indicia 212 can include the words "Trash me," proximately located with the aperture 125 of the disposal receptacle 202, indicating that gloves that have been tried should be deposited there.

In one embodiment, the prospective customer 211 uses the display container 200 by initially withdrawing a glove 210 from the aperture 124 of the dispenser 201. The prospective customer 211 can then try the glove on, as well as examine one or more of the thickness, texture, material, durability, softness, stretchiness, smoothness, and/or coating or additive associated with the glove 210. When finished with this examination, the used glove can be deposited into the aperture 125 of the disposal receptacle 202. Should the glove 210 be suitable for purchase, the prospective customer 211 can select one of the packages 203,204,205,206 from the receiving recess 207.

Figure 3:
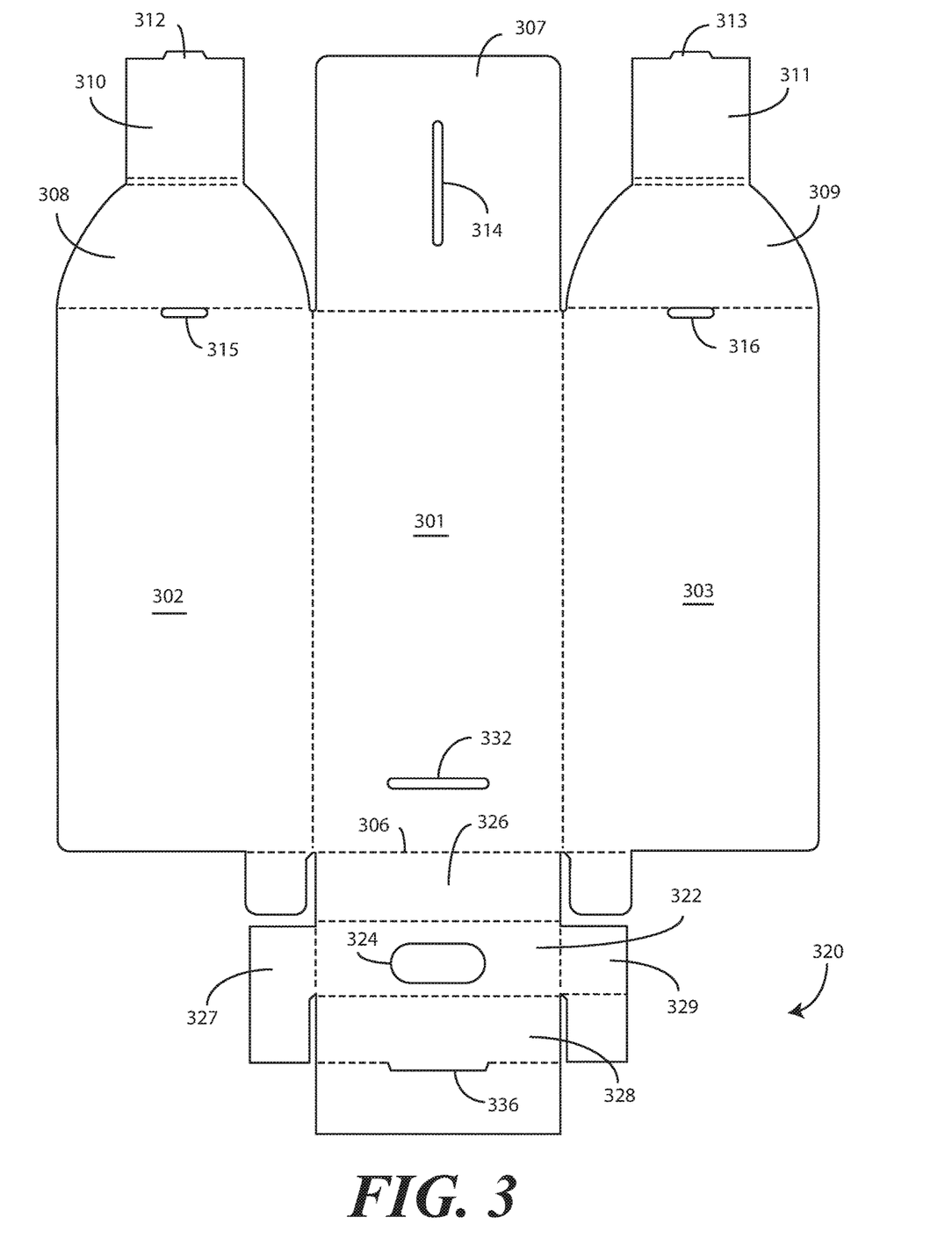
FIG. 3 illustrates another explanatory die template for a display container in accordance with one or more embodiments of the disclosure.

Turning now to FIG. 3, illustrated therein is one explanatory blank 300 suitable for making one or more display containers configured in accordance with one or more embodiments of the disclosure. The blank 300 may be manufactured from any of a variety of materials or combinations of materials, including paper, cardboard, plastic, metal, or fabric. The blank 300 may be of any desired color, and may include printing. Other materials will be obvious to those of ordinary skill in the art having the benefit of this disclosure. The blank 300 may have letters, pictures, logos, designs, instructions for using the contents therein, and/or other markings placed thereon through printing, engraving, molding, or any other suitable method.

In one or more embodiments, a bottom panel 301 is bounded on two sides by a first sidewall 302 and a second sidewall 303. The bottom panel 301 is also bounded by a bottom edge 306 and a rear sidewall 307. Each of the first sidewall 302 and the second sidewall 303 are bounded at the rear of the blank 300 by a first arched partial rear sidewall 308 and a second arched partial rear sidewall 309, respectively.

In this illustrative embodiment, a first tab 310 extends distally from the first arched partial rear sidewall 308, while a second tab 311 extends distally from the second arched partial rear sidewall 309. The first tab 310 terminates in a first insertion tab 312, while the second tab 311 terminates at a second insertion tab 313.

Turning now to the front side of the blank 300, in this illustrative embodiment the bottom panel 301 as a dispenser assembly 320 extending therefrom. The dispenser assembly 320 includes a top panel 322 defining an aperture 324. Extending from the top panel 322 is a first side extension 326 and a second side extension 328. One or more side extensions 327,329 extend from the top panel 322 as well. The bottom panel 301 defines an ovular aperture 332.

When the display container is created, the first sidewall 302 is folded toward the second sidewall 303 until the first sidewall 302 and the second sidewall 303 are substantially orthogonal with the bottom panel 301. The rear sidewall 307 can be folded to be substantially orthogonal with the bottom panel 301 as well. When this occurs, the first arched partial rear sidewall 308 and the second arched partial rear sidewall 309 can be folded toward the rear sidewall 307. The first tab 310 and second tab 311 can be passed through the elongated ovular aperture 314 of the rear sidewall 307. First insertion tab 312 can then be seated in first minor ovular aperture 315, while second insertion tab 313 is situated in second minor ovular aperture 316, thereby constructing the rear side of the display container.

Meanwhile, the first side extension 326, top panel 322, and second side extension 328 can be folded about transverse fold lines, while side extensions 237,239 are tucked in. Insertion tab 336 can be inserted into ovular aperture 332. Accordingly, a dispenser is formed at the front of the display container. The resulting display container is shown in FIG. 4.

Figure 4:
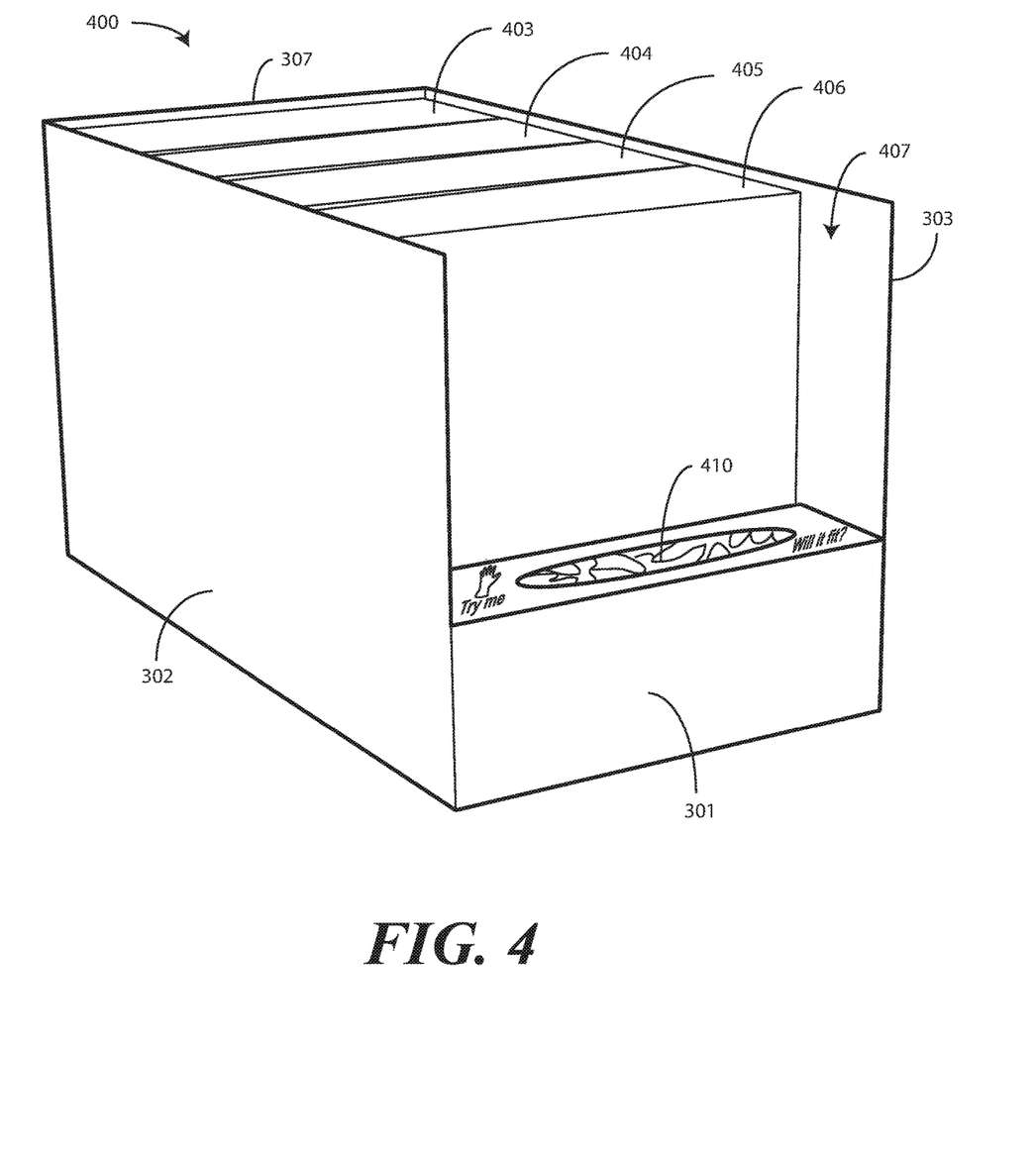
FIG. 4 illustrates another explanatory display container in accordance with one or more embodiments of the disclosure.

Turning now to FIG. 4, illustrated therein is the display container 400 formed from the blank (300) of FIG. 3. As shown the display container 400 includes a first sidewall 302, as second sidewall 303, and a rear sidewall 307. At the front of the display container 400 is the dispenser 401 formed from the dispenser assembly (320). In contrast to the display container (200) of FIG. 2, in the embodiment of FIG. 4, only a dispenser 401 is included, while the disposal receptacle (202) is omitted. Accordingly, the dispenser 401 defines the front side of the display container 400 in this illustrative embodiment.

As shown, one or more packages 403,404,405,406 of products are disposed within a receiving recess 407 defined within the display container 400. In this illustrative embodiment, the packages 403,404,405,406 comprise boxes of gloves. Other containers and other products, suitable for positioning within the receiving recess 407 of the display container 400, will be obvious to those of ordinary skill in the art having the benefit of this disclosure.

To ensure that a prospective customer has the opportunity to examine a glove for proper fit, feature, or other characteristics, in one or more embodiments one or more sample gloves 410 are disposed within the dispenser 401. In one embodiment, the aperture 324 allows one or more gloves 410 to be drawn through the aperture 324 from the dispenser 401. The gloves 410 may comprise medical and/or surgical gloves, or alternatively can be other types of gloves, e.g., non-medical or non-surgical gloves. Still other types of gloves suitable for use with containers configured in accordance with one or more concepts described herein will be obvious to those of ordinary skill in the art having the benefit of this disclosure.

In one embodiment, the number of gloves 410 disposed within the dispenser 401 is related to the number of packages 403,404,405,406. For instance, where there are four packages 403,404,405,406 of gloves in the display container, there may be one to two pairs of gloves 410 within the dispenser. In one embodiment, there is one pair of gloves 410 per package 403,404,405,406 disposed within the dispenser 401. In another embodiment, there are two pairs of gloves 410 per package 403,404,405,406 disposed within the dispenser 401. In yet another embodiment, there are four pairs of gloves 410 per package 403,404,405,406 disposed within the dispenser 401. Accordingly, where the display container 400 includes five packages, there may be a range of ten to twenty gloves 410 disposed within the dispenser 401. Other numbers of sample products disposed within the dispenser 401 will be obvious to those of ordinary skill in the art having the benefit of this disclosure.

Advantageously, the dispenser 401 allows a prospective customer to draw a glove 410 through the aperture 324 of the dispenser 401 to try it on for fit, as well as examine the other physical characteristics of the glove 410 to see if it is suitable for purchase. Advantageously, the aperture 324 of the dispenser 401, combined with the overall weight of the display container 400 when the packages 403,404,405,406 of gloves are disposed therein, allows a single-handed drawing of one or more gloves 410 from the dispenser 401.

Visible indicia 412 can be disposed along the dispenser 401 to indicate the purpose and function of this feature. For example, in one embodiment the visible indicia 412 comprise the words "Try me," with those words disposed near the aperture 324 of the dispenser 401. The visible indicia 412 can also include the words "Will it fit" as well. Other examples of visible indicia 412 will be obvious to those of ordinary skill in the art having the benefit of this disclosure.

In one embodiment, the prospective customer uses the display container 400 by initially withdrawing a glove 410 from the aperture 324 of the dispenser 401. The prospective customer can then try the glove on, as well as examine one or more of the thickness, texture, material, durability, softness, stretchiness, smoothness, and/or coating or additive associated with the glove 410. When finished with this examination, the prospective customer may simply keep the glove 410 as a good will gift from the manufacturer. Should the glove 410 be suitable for purchase, the prospective customer can select one of the packages 403,404,405,406 from the receiving recess 407.

Figure 5:
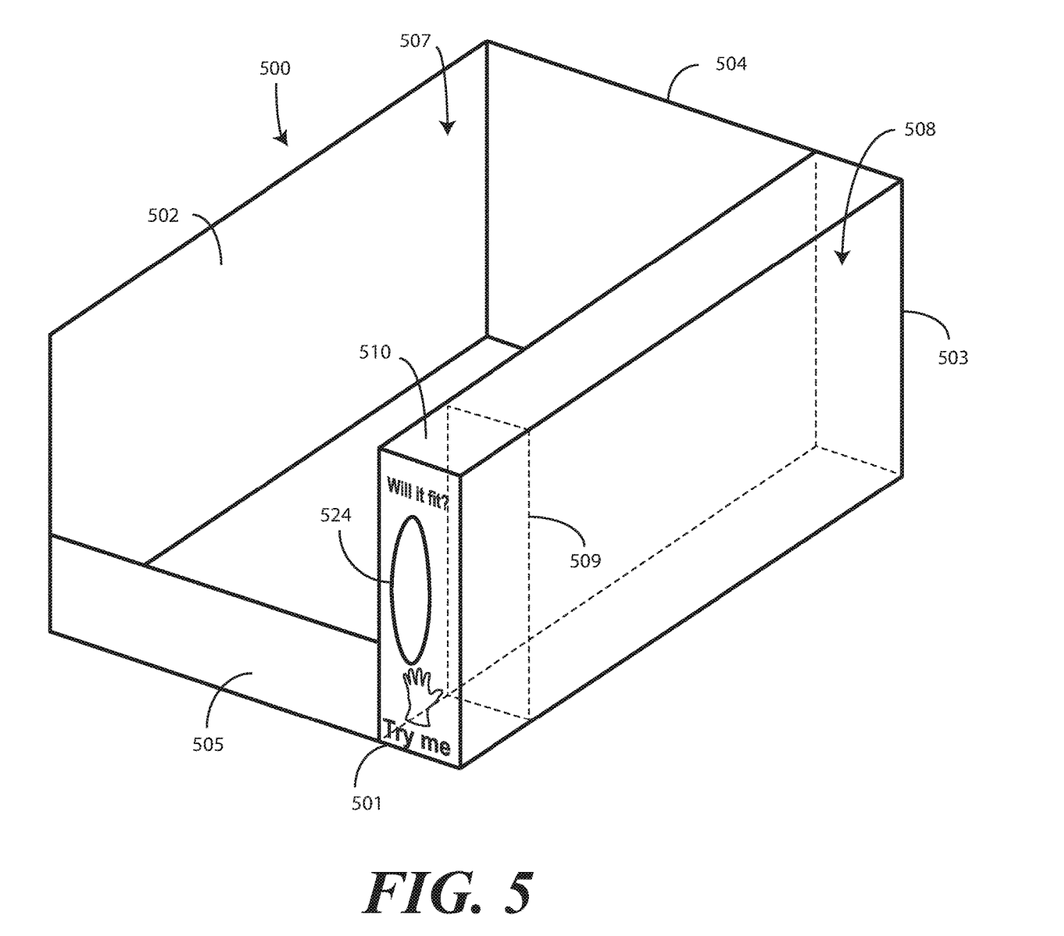
FIG. 5 illustrates yet another explanatory display container in accordance with one or more embodiments of the disclosure.

Turning now to FIG. 5, illustrated therein is another display container 500 configured in accordance with embodiments of the disclosure. As before, the display container 500 includes a first sidewall 502, as second sidewall 503, and a rear sidewall 506. At the front of the display container 500 is a front sidewall 505.

In this illustrative embodiment, rather than defining the front of the display container 500, a dispenser 501 is coupled to the second sidewall 503. In other embodiments, the dispenser 501 could be coupled to the first sidewall 502. As before, one or more packages of products can be disposed within a receiving recess 507 defined within the display container 500. In one embodiment, the packages comprise boxes of gloves. However, other containers and other products can be placed within the receiving recess 507 of the display container 500, as will be obvious to those of ordinary skill in the art having the benefit of this disclosure.

To ensure that a prospective customer has the opportunity to examine a glove for proper fit, feature, or other characteristics, in one or more embodiments one or more sample gloves are disposed within the dispenser 501. An aperture 524 allows one or more gloves to be drawn through the aperture 524 from the dispenser 501. The prospective customer uses the display container 500 by initially withdrawing a glove from the aperture 524 of the dispenser 501. The prospective customer can then try the glove on, as well as examine one or more of the thickness, texture, material, durability, softness, stretchiness, smoothness, and/or coating or additive associated with the glove. When finished with this examination, the prospective customer may simply keep the glove as a good will gift from the manufacturer.

Where the dispenser 501 is disposed along the sidewall of the display container 500, as is the case in FIG. 5, embodiments of the disclosure contemplate that the interior volume 508 of any cavity that runs the length of the sidewall may be larger than necessary for a predefined number of glove samples. Accordingly, in one or more embodiments a wall 509 is disposed within an interior volume 508 to reduce the amount of volume within the dispenser 501. In one or more embodiments, the aperture 524 can initially be covered with a lid or flap 510 that allows for the packing of sample gloves within the dispenser 501.

Figure 6:
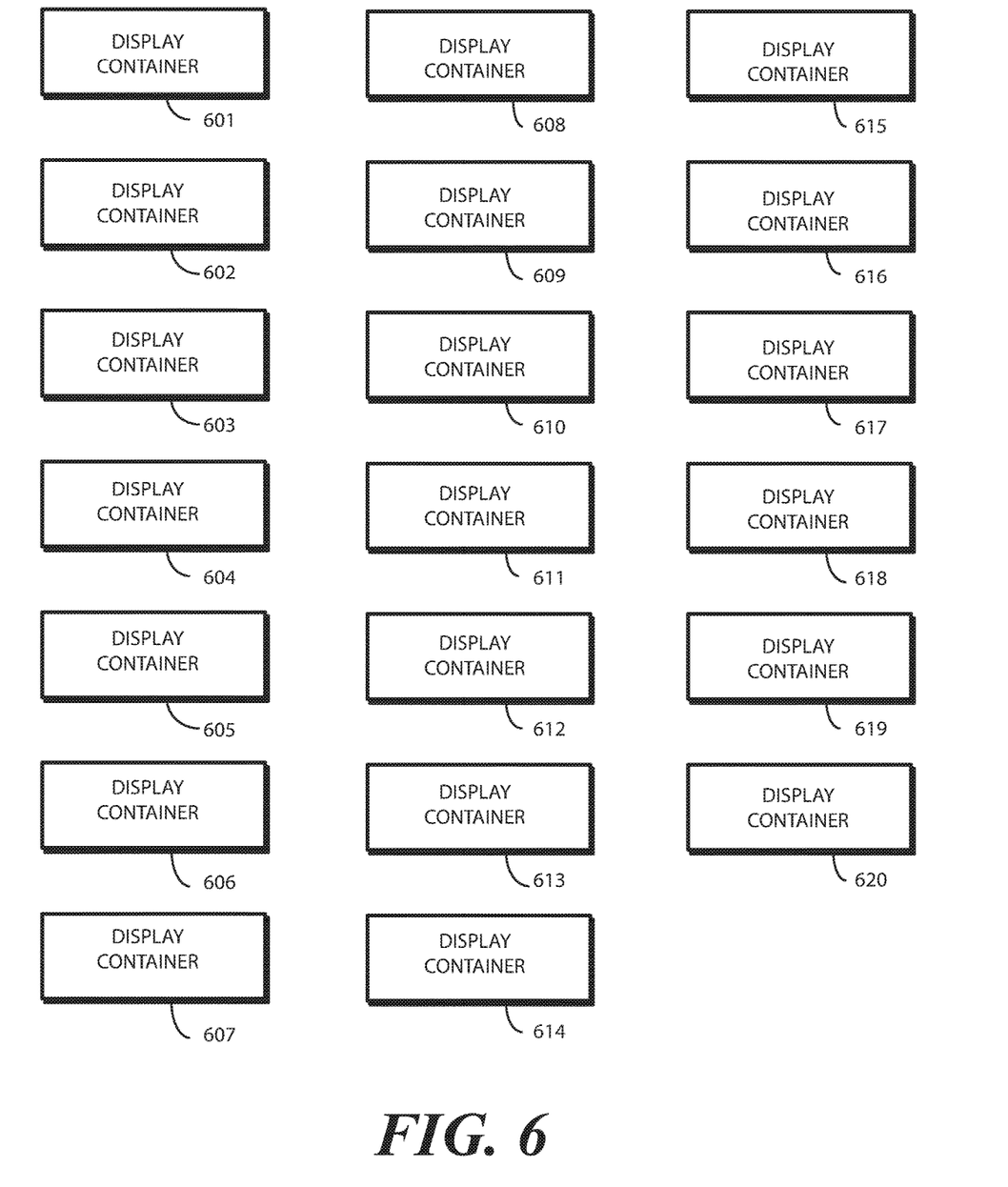
FIG. 6 illustrates one or more embodiments of the disclosure.

Turning now to FIG. 6, illustrated therein are various embodiments of the disclosure. At 601, a display container comprises one or more sidewalls defining a receiving recess. At 601, a dispenser defines a front side of the display container. In one embodiment at 601, the dispenser has a height less than the one or more sidewalls.

At 602, the one or more sidewalls of 601 comprise a first sidewall, a second sidewall, and a rear sidewall. At 603, the dispenser of 601 is disposed between the first sidewall and the second sidewall of 602. At 603, the dispenser of 601 defines an aperture. At 604, the aperture of 603 is ovular.

At 605, the dispenser of 604 further comprises visible indicia indicating a purpose and function of the dispenser. At 607, a plurality of sample product disposed within the dispenser of 604. At 608, the sample product of 607 comprises disposable gloves.

At 609, the display container of 608 further comprises one or more packages of product corresponding to the plurality of sample product of 607, wherein the one or more packages of product are situated within the receiving recess.

At 610, the display container of 601 further comprises a disposal receptacle located adjacent to the dispenser. At 611, the disposal receptacle of 610 defines another aperture. At 612, the display container of 611 further comprises visible indicia indicating that sample product is to be discarded in the disposal receptacle.

At 613, the display container comprises a plurality of sample product disposed within the dispenser. At 614, the display container of 613 further comprises one or more packages of product corresponding to the plurality of sample product, wherein the one or more packages of product are situated within the receiving recess.

At 615, a display container comprises one or more sidewalls defining a receiving recess. At 615, a dispenser is coupled to one sidewall of the one or more sidewalls.

At 616, the one or more sidewalls of 615 comprise a first sidewall, a second sidewall, a rear sidewall, and a front sidewall. At 616, the dispenser is coupled to one of the first sidewall or the second sidewall. At 617, the dispenser of 616 defines an aperture.

At 618, the display container of 617 further comprises a plurality of sample product disposed within the dispenser. At 619, the sample product of 618 comprises disposable gloves. At 620, the display container of 619 further comprises one or more packages of product corresponding to the plurality of sample product, wherein the one or more packages of product are situated within the receiving recess.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. For example, gloves have been used as sample items for illustration. However, display containers in accordance with one or more embodiments of the disclosure can be used to distribute samples of other items as well.

Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A display container, comprising:
one or more sidewalls defining a receiving recess, the one or more sidewalls comprising a first sidewall and a second sidewall; and
a dispenser and a disposal receptacle defining a front side of the display container, wherein the dispenser has a height less than the one or more sidewalls, and wherein the dispenser and the disposal receptacle are both disposed between the first sidewall and the second sidewall.

2. The display container of claim 1, wherein the one or more sidewalls further comprise a bottom panel bounded on two sides by the first sidewall and the second sidewall, wherein the bottom panel bounds a bottom side of both the dispenser and the disposal receptacle.

3. The display container of claim 2, wherein the first sidewall defines a dispenser sidewall and the second sidewall defines a disposal receptacle sidewall.

4. The display container of claim 3, wherein the dispenser comprises a top panel oriented substantially orthogonally with the one or more sidewalls and the front side of the display container, wherein the top panel defines an aperture, wherein the disposal receptacle defines another top panel oriented substantially orthogonally with the one or more sidewalls and the front side of the display container, wherein the another top panel defines another aperture.

5. The display container of claim 4, wherein the aperture is ovular.

6. The display container of claim 4, wherein the dispenser further comprises visible indicia indicating a purpose and function of the dispenser.

7. The display container of claim 4, the display container manufactured from a single folded blank.

8. The display container of claim 7, wherein:
the dispenser comprises:
a side extension extending substantially orthogonally from the top panel and defining a portion of the front side of the display container; and
a front sidewall extending substantially orthogonally from the side extension; and
the disposal receptacle comprises:
another side extension extending substantially orthogonally from the top panel and defining another portion of the front side of the display container; and
another front sidewall extending substantially orthogonally from the another side extension;
wherein the front sidewall and the another front sidewall abut.

9. The display container of claim 8, further comprising:
a plurality of sample product disposed within the dispenser, wherein the plurality of sample product comprises disposable gloves; and
one or more packages of product corresponding to the plurality of sample product, wherein the one or more packages of product are situated within the receiving recess.

10. The display container of claim 1, the disposal receptacle located adjacent to the dispenser.

11. The display container of claim 10, wherein the disposal receptacle defines another aperture.

12. The display container of claim 11, further comprising visible indicia indicating that sample product are to be discarded in the disposal receptacle.

13. The display container of claim 1, further comprising a plurality of sample product disposed within the dispenser.

14. The display container of claim 13, further comprising one or more packages of product corresponding to the plurality of sample product, wherein the one or more packages of product are situated within the receiving recess.

15. A display container, comprising:
one or more sidewalls defining a receiving recess; and
a dispenser and an abutting disposal receptacle coupled between the one or more sidewalls;
wherein:
the one or more sidewalls comprise a first sidewall, a second sidewall, a rear sidewall, and a front sidewall, wherein the dispenser is coupled between the first sidewall and the second sidewall, and the first sidewall, the second sidewall, the rear sidewall, the front sidewall, the dispenser, and the abutting disposal receptacle are defined by a single folded blank; and
the dispenser comprises a top panel defined by the single folded blank, wherein the top panel defines an aperture, and wherein the top panel is oriented substantially orthogonally relative to each of the front sidewall, the rear sidewall, the first sidewall, and the second sidewall.

16. The display container of claim 15, further comprising one or more gloves disposed within the dispenser.

17. The display container of claim 15, further comprising one or more packages situated within the receiving recess.

18. The display container of claim 15, the single folded blank further comprising a first side extension extending substantially orthogonally from the top panel and defining a portion of the front sidewall.

19. The display container of claim 18, wherein the abutting disposal receptacle comprises another top panel oriented substantially parallel with the top panel and another first side extension extending substantially orthogonally from the another top panel and defining another portion of the front sidewall.

20. The display container of claim 19, further comprising a plurality of sample product disposed within the dispenser, wherein the plurality of sample product comprises disposable gloves, further comprising one or more packages of product corresponding to the plurality of sample product, wherein the one or more packages of product are situated within the receiving recess.

* * * * *